United States Patent [19]

Fujii et al.

[11] 4,393,071

[45] Jul. 12, 1983

[54] METHOD OF TREATING GASTRIC, MAMMARY, LUNG AND UTERUS TUMORS

[76] Inventors: Naoharu Fujii, No. 6-10, Jingumae 3-chome, Shibuya-ku, Tokyo; Noboru Iijima, No. 2-1, Kyobashi, Chuo-ku, Tokyo, both of Japan

[21] Appl. No.: 241,308

[22] Filed: Mar. 6, 1981

Related U.S. Application Data

[63] Continuation-in-part of Ser. No. 14,428, Feb. 23, 1979, abandoned, and continuation of Ser. No. 559,018, Mar. 17, 1975, abandoned.

[51] Int. Cl.³ .................... A61K 31/40; A61K 31/555
[52] U.S. Cl. ..................................... 424/274; 424/245
[58] Field of Search ................................. 424/274, 245

[56] References Cited

PUBLICATIONS

Dyer, An Index of Tumor Chemotherapy, 1949, WIH, pp. 10, 11, 97, (2766).

*Primary Examiner*—Jerome D. Goldberg
*Attorney, Agent, or Firm*—McGlew and Tuttle

[57] ABSTRACT

A method of treating malignant tumors by daily administering of between 5 and 100 mg. of protoporphyrin. Preferably the protoporphyrin is given with a carrier which can be a solid edible material.

8 Claims, 5 Drawing Figures

METHOD OF TREATING GASTRIC, MAMMARY, LUNG AND UTERUS TUMORS

RELATIONSHIP TO OTHER APPLICATIONS

This application is a continuation-in-part application of application Ser. No. 014,428 filed on Feb. 23, 1979, and now abandoned, and a continuation application of Ser. No. 559,018 filed on Mar. 17, 1975, also abandoned.

BRIEF SUMMARY OF THE INVENTION

It is a prime object of this invention to provide a method for effectively reducing the growth, metastasis and recurrence of gastric, mammary, lung and uterus tumors by maintaining the regulation of cells in their normal condition or promoting such normalization.

It is another object of this invention to provide a drug useful for reducing growth, metastasis, and recurrence of such tumors.

Other objects, features and merits of this invention will become apparent in the following more detailed description of the invention and from the accompanying drawing which shows graphically the effect of the treatment.

DETAILED DESCRIPTION OF THE INVENTION

Figure 1:
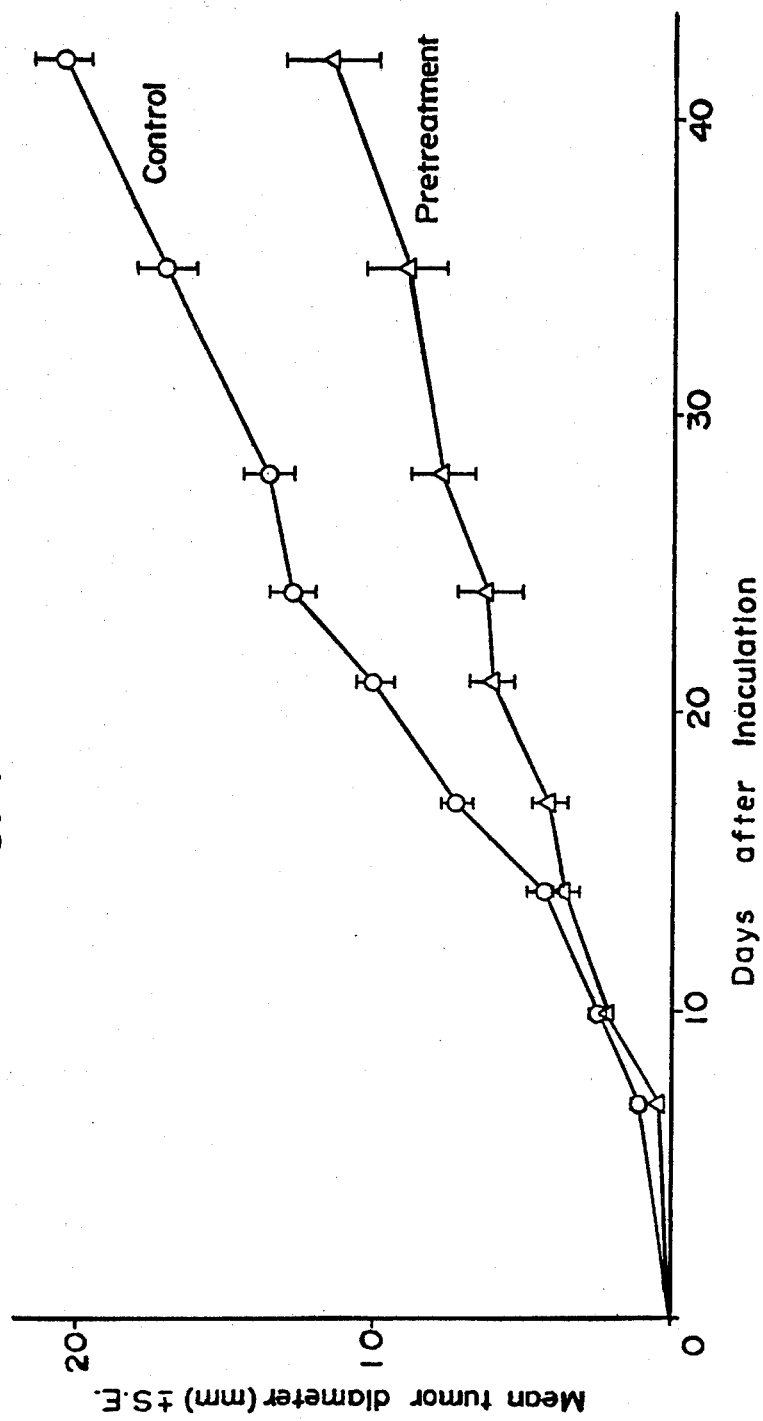
FIGS. 1-5 show various plots useful in explaining the tests of the present invention.

It has been surprisingly found that growth of tumor cells in the subjects observed was significantly controlled or substantially retarded by daily administration of a small amount, for example up to 60 mg. of porphyrin or a metal salt thereof.

In accordance with the present invention, there is thus provided a method for reducing occurrences of gastric, mammary, lung and uterus tumors, or retarding the growth, metastasis and recurrence thereof, comprising daily administering to subjects of a small amount of porphyrin or a metal salt thereof, to thereby maintain the regulation of cells in their normal condition or promoting such normalization.

The word "porphyrin" is a general term for prophyrin and its derivatives and this substance widely occurs in nature as part of the natural body chemicals. Illustrative of the porphyrin substances are, for example, etioporphyrin, mesoporphyrin, protoporphyrin, deuteroporphyrin, hematoporphyrin, coproporphyrin, and uroporphyrin. Examples of metal salts thereof include physiologically acceptable ones such as sodium salts or potassium salts. Examples of metal complexes thereof include physiological acceptables ones such as titanium complex, germanium complex, iron complex, cobalt complex and the sodium or potassium salts of the said metal complexes.

A preferred porphyrin is the sodium salt of protoporphyrin ($C_{34}H_{32}N_4O_4Na_2$) and is commercially available under various drug names. Although porphyrin is now used for treating certain kinds of liver diseases such as hepatitis it has not been used on a regular basis for the normalization of body functions. Porphyrin, however, is already confirmed as being harmless to humans.

Based on extensive research on protoporphyrin, it has been concluded that in the human body this substance chiefly promotes the release of a regulator in the lymphatic system and controls the occurrence and growth of tumors which is against homeostasis inherent in the body. The lymphatic system functions to maintain various internal organs in a definite size. In the present invention, the effect achieved by the use of a porphyrin is brought about through this action. Other diseases such as lymphomas, leukemias, and hypertension may also be treated by the use of porphyrin in accordance with the method of this invention.

According to this invention, the porphyrin drug is administered orally, either alone or as a mixture with one or more carriers, in the form of a tablet, pill, powder or capsule or parenterally by intramuscular or intravenous injection in the form of a solution.

To facilitate or insure daily administration, the drug may be incorporated into a liquid or solid edibles, for example, milk, rice or sweets such as chewing-gum and candies. As the porphyrin itself is stable at high temperatures, it may also be incorporated into bread or the like.

No particular limitations exists in the maximum daily dosage of porphyrin, since a significantly excess quantity of porphyrin gives no harmful effect on the human body. From the economical point of view, however, porphyrin is advantageously administered in a daily dosage of less than 100 mg. and usually less than 60 mg. The minimum daily dosage of porphyrin is usually at least 5 mg. and preferrably 10 mg. to produce sufficient effectiveness on the human body. It is of course to be understood that the daily dosage may exceed the above defined extent in special cases. A clinical measurement showed that when an administered dosage was about 20 mg. a day, the entire quantity was excreted in the bile within 24 hours without leaving any trace of the drug.

The invention will now be illustrated in more detail by way of the following examples.

EXAMPLE 1

Using mice as the test animal, an experiment was first carried out to prove the reducing or retarding effect of the porphyrin drug on the growth of a tumor. Two groups of mice, each consisting of twenty mice, were used in the experiment. Mice of one group received for 3 weeks a preliminary daily treatment of injections of 0.05 mg. of sodium salt of protophyrin as the porphyrin drug in a physiological saline solution, while those of the other group did not receive such a prelininary treatment.

A malignant tumor MH 134 (a transplanted cancer of a liver cancer origin) was then transplanted into the mice of both groups. All of the mice were then bred under the same conditions. Table 1 shows the survival ratio of the mice after transplantation.

TABLE 1

| Time elapsed (week) | Treated Number of survivals | Treated Survival ratio (%) | Not treated Number of survivals | Not treated Survival ratio (%) |
| --- | --- | --- | --- | --- |
| 1 | 17 | 85 | 9 | 45 |
| 2 | 15 | 75 | 7 | 35 |
| 3 | 11 | 55 | 5 | 25 |
| 4 | 11 | 55 | 2 | 10 |

FIG. 1 shows, for this experiment, the change in size of the transplanted cancer as a function of the lapse of time.

Swelling of cancer in the human body is caused not only by a higher growth rate of the cancerous cells, but also a failure of prompt treatment for dead cancerous cells. It is known that cancerous cells have a definite life span and eventually die, and that a cancer becomes larger when the dead cancerous cells are not sufficiently treated in vivo. A reason why the results of treatment of rectal cancer has not been satisfactory is chiefly ascribable to the fact that the treating capacity for dead cancerous cells becomes poor.

As a standard for evaluating the result of treatment for dead cancerous cells in vivo, the factor of "cell loss" is introduced and was measured according to the following method:

As described in the abovementioned test, two groups of mice, each consisting of 20 mice, were used as the test animals. Mice of one group received daily injections of 10 mg. of protoporphyrin (PPN) for 3 weeks, while those of the other group did not. All the mice of the two groups were then innoculated with $4 \times 10^6$ or $4 \times 10^4$ ascites tumor cells. A potential doubling time (P) and an actual doubling time (A) were measured for the mice of both groups and "cell loss" was then calculated from these values according to the following Steel's equation:

$$\text{Cell loss} = 1 - P/A$$

wherein
P is the potential doubling time, i.e. the theoretically calculated time required for doubling tumor cells, and
A is the Actual doubling time, i.e. the actual time required for doubling tumor cells.

The results of the rests are tabulated in Tables 2 and 3 below:

TABLE 2

INOCULATED TUMOR CELLS ($4 \times 10^6$)

|  | Potential doubling time (P) | Actual doubling time (A) | P/A (%) | Cell loss (%) |
|---|---|---|---|---|
| Not treated (control) | 23.7 | 44.6 | 53.1 | 46.9 |
| Treated with PPN | 22.9 | 61.7 | 37.1 | 62.9 |

TABLE 3

INOCULATED TUMOR CELLS ($4 \times 10^4$)

|  | Potential doubling time (%) | Actual Doubling time (%) | P/A (%) | Cell loss |
|---|---|---|---|---|
| Not treated (control) | 20.4 | 50.8 | 40.2 | 59.8 |
| Treated with PPN | 15.7 | 100.0 | 15.7 | 84.3 |

The above tables show that the "cell loss" values for the mice treated with protoporphyrin according to this invention is remarkably large as compared with those not treated. Increase in the "cell loss" value suggests that the protoporphyrin promotes a regulation of the tumor cells in vivo, up to the level in the normal tissues.

A considerable number of tests were also carried out on humans. Some of these tests will be described.

EXAMPLE 2

A group of 30 humans all between the ages of 50 and 60 years old, 10 of whom were female, were selected. All of the patients suffered from Borman III-type gastric cancer. All of the patients had surgery. The patient were selected at random. The patients were divided into two groups. Half of the patients were used as a control group and were given 5 FU (5-Fluorouracil) at a dosage of 200 mg/day. The other 15 patients were given protoporphyrin (PPN) at 2 mg/day. The PPN was given in the form of a tablet and was given after the meal once each day. All medicines given were given daily until the patient died.

Figure 2:
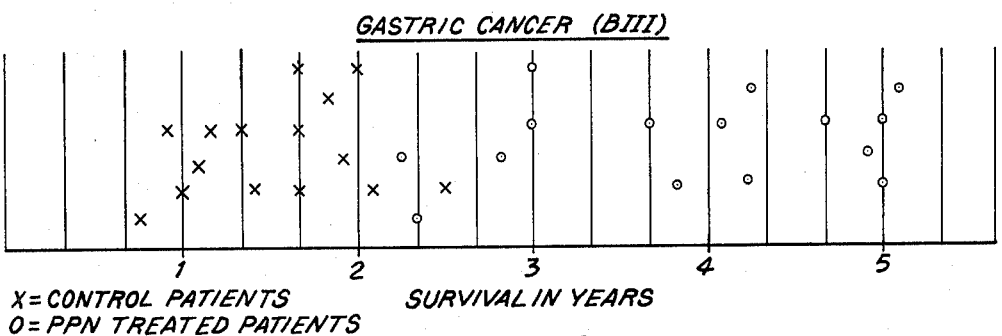

Referring to FIG. 2, there is shown a result of the test wherein the abscissa stands for survival years. The cases are plotted vertically spread apart only for ease of separating the test results. The vertical spacing, however, has no significance and is used only for ease of description.

As is shown, each of the control patients survived between a period of less than 1 year and up to a maximum of about 2½ years following surgery. On the other hand, the patients given the PPN are shown to survive from a minimum of approximately 2⅓ years up to 5 years, with two of these patients still being alive as of the date of this application. The mean survival time for the control patients was 1 year, 6 months while for those patients given the PPN treatment, the mean survival time was 3 years and 2 months, representing approximately 2½ times improvement over the control patients.

EXAMPLE 3

20 patients having mammary cancer in Stage II were randomly selected. Patients were between the ages of 40 and 50 years old. Surgery was made on each of the patients prior to the present tests. The patients were selected at random. 10 of the patients were retained as a control and were given X-ray irradiation of 2,000 R. The other 10 patients were given 20 mg/day PPN each day in addition to the X-ray irradiation at 2,000 R. The PPN was given in the form of a tablet and was given once a day after the meal. The PPN was given daily until the patients died.

Figure 3:
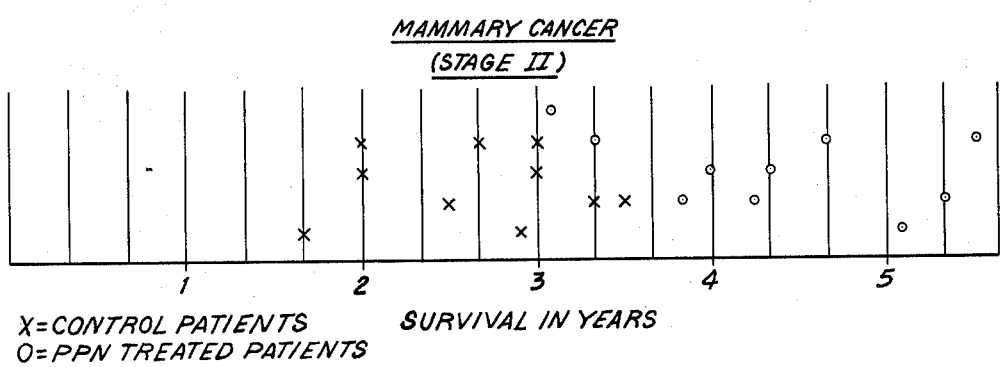

With reference now to FIG. 3, there is shown a plot of the number of years of survival counted from the time of the surgery. As is noted, the patients in the control group survived from between 1⅔ years up to approximately 3½ years. The patients given the PPN treatment survived from about 3 years to more than 5 years. The mean survival time for the control patients were 2 years and 8 months while the mean survival time for the patients given PPN was 4 years and 4 months, which is about 1.6 times as much. Two of the patients are still alive as of the date of this application.

EXAMPLE 4

20 human patients of between 40 and 50 years old were selected all of whom had lung cancer. 5 of the patients were female. The patients each had operations performed on them and after the operation, were divided into 2 groups. 10 of the patients represented a control group and received X-ray irradiation following the operation. The other 10 were given 20 mg/day of PPN in addition to the X-ray irradiation. The PPN was given in the form of tablets and was given once a day after each meal. The PPN was given continuously until the patients died.

Figure 4:
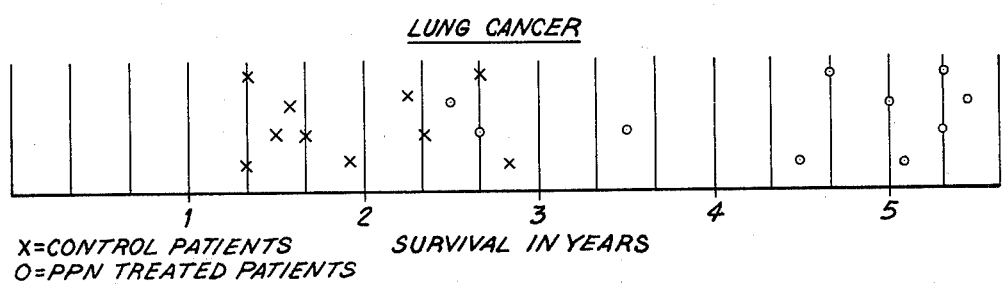

As shown in FIG. 4, the control patients survived following the operation from between 1⅓ years up to almost 3 years. The patients given the PPN treatment survived from between 2 and ½ years until after 5 years. The mean survival time for the control patients was 1 year 11 months. For the patients in the PPN group the mean survival time was 4 years 4 months, about 2.3 times better than the control patients. Two of these patients are still alive as of the date of this application.

EXAMPLE 5

20 patients of between 40 and 60 years old were selected having uterus cancer. In this case inoperative patients were selected at random. The patients were divided into two groups. The first group consisted of 10 patients in a control group and they were given X-ray irradiation of 1,000 R. The treated patients were given 20 mg/day of PPN. The PPN was given in the form of tablets once a day after each meal. The PPN was given daily until the patients died.

Figure 5:
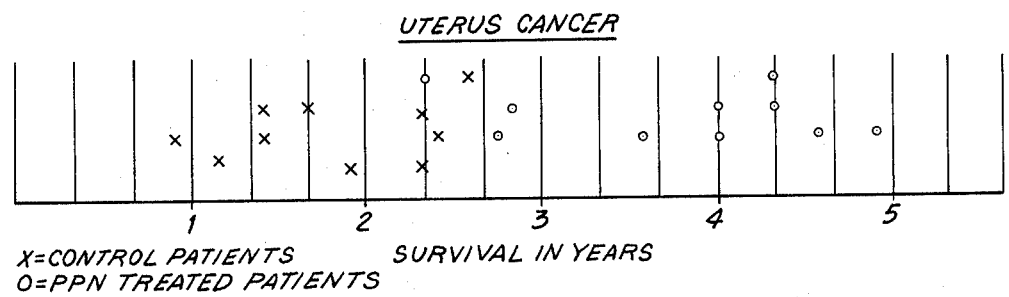

Referring now to FIG. 5 there is shown the survival time for these 20 patients. In this case survival time is calculated after the judgement of inoperativeness of each patient. It is noted, that the control patients survived from between approximately 1 year and $2\frac{2}{3}$ years while the patients given the PPN survived between $2\frac{1}{3}$ years up to 5 years. The mean survival time for the control patients was 1 year 10 months while the mean survival time for the PPN Patients was 3 years 9 months, about 2 times improvement over the control patients. One patient is still alive as of the date of this application.

In addition to each of the above tests, there were additional cases and tests carried out. By way of example, the following are some individual cases.

A female age 42 had a surgical removal of a mammary cancer with the removal of all the occupying lymphatic system and some muscles, because of the fear of recurrence or metastasis. The subject had lymphatic swellings of the whole body.

During the first week, 20 mg. of the drug was daily administered, orally, 10 mg. in the morning and another 10 mg. 12 hours later.

During the second week, 30 mg. of the drug in three equal portions was given orally everyday. It was noted that the lymphatic swellings were becoming smaller and the swelling glands of the right armpit nearly disappeared. The subject's appetite had increased, her sleep increased, and generally her condition was improved. Thereafter, the dosage was reduced to 20 mg. given orally, 10 mg in the morning and 10 mg. in the evening. All lymphatic swellings had disappeared. The dosage was continued thereafter in order to retard any recurrence. No ill side effects had been noted.

Another subject, a female aged 72 had a tumor of the bladder. Chemotherapeutic treatments were used and produced several bad side effects such as pain, bleeding and fatigue. The bleeding occurred not only in the urine, but also in the mouth and throat.

During the first week, 20 mg. of the drug was daily administered orally in two equal portions in a suspension of chemotherapeutic drugs. After 3 days, the bleeding was stopped. There were no side effects and the pain was relieved.

During the second and third weeks, the dosage of the drug was increased to 30 mg. given in three equal portions every day.

Three female subjecrs each had a mammary tumor and indicated metastasis of the armpit. The first subject, aged 53, had the drug administered in equal dosages twice a day for a total of 20 mg. She survived for two years. The second subject, aged 43, had the dosage orally administered three times a day with 20 mg. being given at night and 10 mg. being given at two other times for a total dosage of 40 mg. a day, After 2 years 3 months, the subject was still alive. The third subject had a "Jones" operation (radical operation) and metastasis of the right armpit. The drug was administered in an amount of 20 mg. a day in two equal dosages for the first three months, and thereafter increased to 30 mg. a day in 3 equal 10 mg. dosages. The subject was still alive $1\frac{1}{2}$ years after commencing administration of the drug.

A male subject, aged 56, had a stomach cancer which could not be operated upon. During the first 6 months, he orally received 60 mg. of the drug in three equal dosages during the day. This amount was then decreased down to 30 mg. during the succeeding six months and thereafter was maintained at 20 mg. The subject was still alive after two years had elapsed since administration of the drug was commenced.

A male aged 18 had an osteocarcinoma and was operated therefor. The drug was administered in two equal daily dosages totallying 20 mg. No side effects had been noted and the subject was still alive three years after commencement of taking the drug.

A male subject aged 63 had stomach cancer. Because of the patient's debilitated condition, a surgical operation was not advised. An X-ray observation showed a cancer progressing. The subject had the drug administered orally, 20 mg. a day, in two 10 mg. dosages. After three months of administering the drug, no further process of the cancer was shown by X-ray pictures.

It should be noted, that the effect of PPN for humans having malignant tumors in the terminal stage has been tested in the hospital of St. Marianna University, for the past four years. On the average, those given PPN lived approximately five times as long as the patients not receiving PPN. The test was carried out for 98 tumor bearers of stomach, lung, womb, liver and pancreas types of cancer. In each case, the surgical removal and radiology treatments were found ineffective.

Of the 98 patients, 48 patients were given PPN in the amounts of 20–30 mg./day. The average survival rate for the patients receiving PPN was 201 days, which was approximately five times that of the control which was 43 days. The longest survival days in the control was 174 days while in the PPN group 14 patients lived as much as 487 days, five of them are still living as of the date of this application.

The length of survival rate varied in accordance with the type of tumor. For example, those having tumor in the womb appear to have the longest survival rate and the greatest improvement over the control group. Approximately 11 times the average survival rate was found in the PPN group as compared to the control group. In the case of the breast cancer, liver or pancreas cancer, the improvement is approximately 5 times as great. In stomach cancer, it is approximately 2.5 times as great and in lung cancer it is approximately 1.5 times as great.

Throughout this application the term cancer and the term malignant tumors are used synomously and should be understood as meaning the same thing.

There has been disclosed heretofore the best embodiment of the invention presently contemplated. However, it is to be understood that various changes and modifications may be made thereto without departing from the spirit of the invention.

We claim:

1. A method of treating in an animal body malignant tumors selected from the group consisting of gastric tumor, mammary tumor, lung tumor, and uterus tumor, comprising the step of daily administering to the animal body of between 5 to 100 mg. of protoporphyrin.

2. A method according to claim 1 wherein said protoporphyrin is administered in a physiologically acceptable salt selected from the group consisting of sodium salt and potassium salts.

3. A method according to claim 1, wherein said protoporphyrin is administered in the form of a composition with a carrier.

4. A method according to claim 3, wherein said carrier is solid.

5. A method according to claim 4, wherein said carrier is a solid edible material.

6. A method according to claim 3, wherein said carrier is a liquid.

7. A method according to claim 1, wherein said protoporphyrin is administered in a physiologically acceptable complex selected from the group consisting of titanium complex, iron complex, cobalt complex, germanium complex and their sodium or potassium salts.

8. A method according to claim 1 wherein said protoporphyrin is given in the amount of 20 mg./day.

* * * * *